(12) United States Patent
Nemerson et al.

(10) Patent No.: US 7,045,350 B2
(45) Date of Patent: May 16, 2006

(54) ALTERNATIVELY SPLICED CIRCULATING TISSUE FACTOR

(75) Inventors: Yale Nemerson, New York, NY (US); Vladimir Bogdanov, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 643 days.

(21) Appl. No.: 10/230,839

(22) Filed: Aug. 29, 2002

(65) Prior Publication Data

US 2003/0049784 A1   Mar. 13, 2003

Related U.S. Application Data

(60) Provisional application No. 60/316,244, filed on Aug. 30, 2001.

(51) Int. Cl.
    *C12N 5/00*    (2006.01)
(52) U.S. Cl. ................. 435/325; 435/252.3; 435/320.1; 536/23.1; 530/350; 530/300; 530/387.1
(58) Field of Classification Search ................. 435/325, 435/252.3, 320.1; 536/23.1; 530/300, 350, 530/387.1
    See application file for complete search history.

(56) References Cited

U.S. PATENT DOCUMENTS

| | | | |
|---|---|---|---|
| 3,625,214 | A | 12/1971 | Higuchi |
| 4,244,946 | A | 1/1981 | River et al. |
| 4,305,872 | A | 12/1981 | Johnston et al. |
| 4,316,891 | A | 2/1982 | Guillemin et al. |
| 4,629,784 | A | 12/1986 | Stammer |
| 4,789,734 | A | 12/1988 | Pierschbacher |
| 4,792,525 | A | 12/1988 | Ruoslaghti et al. |
| 4,868,116 | A | 9/1989 | Morgan et al. |
| 4,906,474 | A | 3/1990 | Langer et al. |
| 4,925,673 | A | 5/1990 | Steiner et al. |
| 4,980,286 | A | 12/1990 | Morgan et al. |
| 5,211,947 | A | 5/1993 | Brannan et al. |
| 5,346,991 | A | 9/1994 | Roy et al. |
| 5,510,466 | A | 4/1996 | Krieger et al. |
| 5,585,479 | A | 12/1996 | Hoke et al. |
| 5,652,224 | A | 7/1997 | Wilson et al. |
| 5,746,223 | A | 5/1998 | Williams |
| 5,925,333 | A | 7/1999 | Krieger et al. |

FOREIGN PATENT DOCUMENTS

| | | |
|---|---|---|
| EP | 0 347 262 | 12/1989 |
| JP | 03 290184 | 12/1991 |
| JP | 05 192179 | 11/1993 |
| WO | WO 90/05748 | 5/1990 |
| WO | WO 93/01286 | 1/1993 |
| WO | WO 93/19166 | 9/1993 |
| WO | WO 96/00288 | 1/1996 |

OTHER PUBLICATIONS

Chinnalyan et al. 1995; Cell 81:505-512.*
*Abdulkadir, et al., "Tissue factor expression and angiogenesis in human prostate carcinoma," Hum. Pathol. 31: 443-447 (2000).
*Agnelli, et al., Blood 96: 491 (2000) abstract only.
Agrawal, et al., "Oligodeoxynucleoside phosphoramidates and phosphorothioates as inhibitors of human immunodeficiency virus," Proc Natl Acad Sci 7079-7083 (1988).
*Atsumi, et al., "Up-regulated tissue factor expression in antiphospholipid syndrome," Thromb. Haemost. 77:222-223 (1997).
*Bach, et al., "Factor VII binding to tissue factor in reconstituted phospholipid vesicles: induction of cooperativity by phosphatidylserine," Biochemistry 25(14): 4007-4020 (1986).
*Belch, "The role of the white blood cell in arterial disease," Blood Coagul. Fibrinolysis 1: 183-192 (1990).
Blume, et al., "Triple helix formation by purine-rich oligonucleotides targeted to the human dihydrofolate reductase promoter," Nucl. Acids Res. 20:1777-1784 (1992).
Camerer, et al., "Binding of factor VIIa to tissue factor on keratinocytes induces gene expression," J. Biol. Chem. 275(9): 6580-6585 (2000).
Clackson, et al., "Making antibody fragments using phage display libraries," Nature 352: 624-628 (1991).
*Clauss, et al., "Vascular permeability factor: a tumor-derived polypeptide that induces endothelial cell and monocyte procoagulant activity, and promotes monocyte migration," J. Exp. Med. 172(6): 1535-1545 (1990).
*Combes, et al., "In vitro generation of endothelial microparticles and possible prothrombotic activity in patients with lupus anticoagulant," J. Clin. Invest. 104(1): 93-102 (1999).

(Continued)

*Primary Examiner*—Karen Cochrane Carlson
(74) *Attorney, Agent, or Firm*—Pabst Patent Group LLP

(57) ABSTRACT

A new circulating form of soluble human tissue factor was identified. This new form of human tissue factor appears to be the result of alternative splicing and is therefore referred to as "alt-hTF." Alt-hTF mRNA was detected in a cell line, HL-60. The cDNA region encoding the entire open reading frame of alt-hTF was cloned. The sequence encoding the alt-hTF mature peptide was expressed in bacteria. alt-hTF consists of the first 166 amino acids of membrane bound TF, and a 40 amino acid C-terminal region unique to alt-hTF. Alt-hTF is likely to be a useful target for compounds to inhibit clotting and to treat disorders associated with elevated TF. It may also be useful as a target for antibodies selectively reactive with alt-hTF, to remove it from the circulation for treatment of clotting or other disorders associated with elevated or abnormal levels of TF, including thrombotic conditions, cardiovascular disorders, DVT, DIC, and possibly metastatic cancers.

15 Claims, 4 Drawing Sheets

OTHER PUBLICATIONS

Cooney, et al., "Site-specific oligonucleotide binding represses transcription of the human c-myc gene in vitro," Science 241: 456-459 (1988).

*Corre, et al., "Smoking and leukocyte-counts. Results of an epidemiological survey," Lancet 2: 632-634 (1971).

Crooke, "Progress toward oligonucleotide therapeutics: pharmacodynamic properties," FASEB J. 7: 533-539 (1993).

Daugherty, et al., "Polymerase chain reaction the cloning, CDR-grafting, and rapid expression of a murine monoclonal antibody directed against the CD18 component of leukocyte integrins," Nucl. Acids Res. 19(9): 2471-2476 (1991).

Donze, et al., "RNA interference in mammalian cells using siRNAs synthesized with T7 RNA polymerase," Nucl. Acids Res. 30(10): e46 (2002).

Duval-Valentin, et al., "Specific inhibition of transcription by triple helix-forming oligonucleotides," Proc. Natl. Acad. Sci. USA 89: 504-508 (1992).

*Dvorak, et al., "Fibrin as a component of the tumor stroma: origins and biological significance," Cancer Metastasis Rev 2: 41-73 (1983).

*Fidler, "Tumor heterogeneity and the biology of cancer invasion and metastasis," Cancer Res. 38(9): 2651-2660 (1978).

*Folkman, "Seminars in Medicine of the Beth Israel Hospital, Boston. Clinical applications of research on angiogenesis," N. Engl. J. Med. 333: 1757-1763 (1995).

*Friedman, et al., "The leukocyte count as a predictor of myocardial infarction," N. Engl. J. Med. 290(23): 1275-1278 (1974).

*Gando, et al., "Significant correlations between tissue factor and thrombin markers in trauma and septic patients with disseminated intravascular coagulation," Thromb. Haemost. 79(6): 1111-1115 (1998).

Giesen, et al., "Blood-borne tissue factor: another view of thrombosis," Proc. Natl. Acad. Sci. USA 96(5): 2311-2315 (1999).

Gregoriadis, "Liposomes" In *Drug Carriers in Biology and Medicine*, Chapter 14, Academic Press, pp. 287-341 (1979).

Grigoriev, et al., "A triple helix-forming oligonucleotide-intercalator conjugate acts as a transcriptional repressor via inhibition of NF KB binding to interleukin-2 receptor a-regulatory sequence," J. Biol. Chem. 267:3389-3395 (1992)

Guo, et al., "Effect of all-trans retinoic acid and arsenic trioxide on tissue factor expression in acute promyelocytic leukemia cells," Chin. Med. J. 114(1): 30-34 (2001).

Guo, et al., "Effect of all-trans retinoic acid and arsenic trioxide on tissue factor expression in NB4 cells," Chin. J. Hematol. 20(9): 453-455 (1999).

*Hathcock, et al., Thromb. Haemost. Supplement, Abstract OC2404 (2001).

Holen, et al., "Positional effects of short interfering RNAs targeting the human coagulation trigger tissue factor," Nucl. Acids Res. 30(8):1757-1766 (2002).

Holt, et al., "An oligomer complementary to c-myc mRNA inhibits proliferation of HL-60 promyelocytic cells and induces differentiation," Mol. Cell. Biol. 8: 963-973 (1988).

*Hu, et al., "Procoagulant activity in cancer cells is dependent on tissue factor expression," Oncol. Res. 6(7): 321-327 (1994).

Itakura, et al., "Synthesis and use of synthetic oligonucleotides", in *Ann. Rev. Biochem.* 53: 323-356 (1984).

Kabat, et al., Sequences of Proteins of Immunological Interest, 4th ed. (U.S. Dept. Health and Human Services, Bethesda, MD (1987).

*Key, et al., "Whole blood tissue factor procoagulant activity is elevated in patients with sickle cell disease," Blood 91(11): 4216-4223 (1998).

*Kim, et al., "Changes of plasma tissue factor and tissue factor pathway inhibitor antigen levels and induction of tissue factor expression on the monocytes in coronary artery disease," Cardiology 93(1-2): 31-36 (2000).

Leadley, et al. "Contribution of in vivo models of thrombosis to the discovery and development of novel antithrombotic agents," J. Pharmacol. Toxicol. Methods 43(2):101-16 (2000).

Leatham, et al., "Increased monocyte tissue factor expression in coronary disease," Br. Heart J. 73(1): 10-13 (1995).

*Lee, et al., "Activation of monocytes, T-lymphocytes and plasma inflammatory markers in angina patients," Exp. Mol. Med. 31(3): 159-164 (1999).

*Lowe, et al., "White blood cell count and haematocrit as predictors of coronary recurrence after myocardial infarction," Thromb. Haemost. 54(3): 700-703 (1985).

Maher, et al., "Inhibition of DNA Binding Proteins by Oligonucleotide-Directed Triple Helix Formation," Science 245: 725-730 (1989).

*Mallat, et al., "Elevated levels of shed membrane microparticles with procoagulant potential in the peripheral circulating blood of patients with acute coronary syndromes," Circulation 101(8): 841-843 (2000).

*Matetzky, et al., "Smoking increases tissue factor expression in atherosclerotic plaqueus: implications for plaque thrombogenicity," Circulation 102(6) : 602-604 (2000).

Merrifield, "Solid Phase Peptide Synthesis. I. The Synthesis of a Tetrapeptide," J. Am. Chem. Soc. 85:2149-2154 (1963).

Misumi, et al., "Comparison of plasma tissue factor levels in unstable and stable angina pectoris," Am. J. Cardiol. 81(1): 22-26 (1998).

*Moreno, et al., "Macrophages, smooth muscle cells and tissue factor in unstable angina. Implications for cell-mediated throm in acute coronary syndromes," Circulation 94(12): 3090-3097 (1996).

*Morrissey, et al., "Quantitation of activated factor VII levels in plasma using a tissue factor mutant selectively deficient in pro factor VII activation," Blood 81: 734-744 (1993).

Mulligan, "The basic science of gene therapy," Science 260: 926-932 (1993).

*Murray, "Coagulation and cancer," Br. J. Cancer 64(3): 422-424 (1991).

Narang, et al., in "Chemical Synthesis of Deoxyoligonucleotides by the Modified Triester Method," Methods Enzymol. 65:610-6.

*Nieuwland, et al., "Cellular origin and procoagulant properties of microparticles in meningococcal sepsis," Blood 95(3): 930-9.

*Novina, et al., "siRNA-directed inhibition of HIV-1 infection," Nature Med. 8(7): 681-686 (2002).

*Oemar, et al., "Human connective tissue growth factor is expressed in advanced atherosclerotic lesions," Circulation 95(4):83 (1997).

Offensperger, et al., "In vivo inhibition of duck hepatitis B virus replication and gene expression by phosphorothioate modifi antisense oligodeoxynucleotides," EMBO J. 12:1257-1262 (1993).

Orson, et al., Oligonucleotide inhibition of IL2RV mRNA transcription by promoter region collinear triplex formation in lymphoc Acids Res. 19:3435-3441 (1991).

Pendurthi, et al., "Factor VIIa and thrombin induce the expression Cyr61 and connective tissue growth factor, extracellular signaling proteins that could act as possible downstream mediators in factor VIIa x tissue factor-induced signal transduction," J. I 275(19): 14632-14641 (2000).

Postel, et a l., "Evidence that a triplex-forming oligodeoxyribonucleotide binds to the c-myc promoter in HeLa cells, thereby reducing c-myc mRNA levels," Proc. Natl. Acad. Sci. USA 88(18): 8227-8231 (1991).

*Rickles, et al., "Activation of blood coagulation in cancer: Trousseau's syndrome revisited," Blood 62: 14-31 (1983).

Sarin, et al., "Inhibition of acquired immunodeficiency syndrome virus by oligodeoxynucleoside methylphosphonates," Proc. Natl. Acad. Sci. USA 85: 7448-7794 (1989).

*Sharp, "RNA interference—2001," Genes Devel. 15(5): 485-490 (2001).

Shaw, et al., "Modified deoxyoligonucleotides stable to exonuclease degradation in serum," Nucleic Acids Res. 19:747-750 (1991).

Shimura, et al., "Plasma tissue factor and tissue factor pathway inhibitor levels in patients with disseminated intravascular coagulation," Amer. J. Hematol. 55(4): 169-174 (1997).

*Soejima, et al., "Heightened tissue factor associated with tissue factor pathway inhibitor and prognosis in patients with unstable angina," Circulation 99(22): 2908-2913 (1999).

*Soejima, et al., "Angiotensin-converting enzyme inhibition reduces monocyte chemoattractant protein-1 and tissue factor levels in patients with myocardial infarction," J. Am. Coll. Cardiol. 34(4): 983-988 (1999).

Stent & Calender, Molecular Genetics, W.H. Freeman & Co., pp. 213-219 (1971).

*Suefuji, et al., "Increased plasma tissue factor levels in acute myocardial infarction," Am. Heart J. 134(2.1): 253-259 (1997).

Sui, et al., "A DNA vector-based RNAi technology to suppress gene expression in mammalian cells," Proc. Natl. Acad. Sci. USA 99(8): 5515-5520 (2002).

Szostak, "In vitro genetics," TIBS 17:89-93 (1992).

*Takano, et al. "Tissue factor, osteopontin, alphavbeta3 integrin expression in microvasculature of gliomas associated with vascular endothelial growth factor expression," Br. J. Cancer 82(12) : 1967-1973 (2000).

Wickstrom, et al., "Human promyelocytic leukemia HL-60 cell proliferation and c-myc protein expression are inhibited by an antisense pentadecadeoxynucleotide targeted against c-myc mRNA," Proc. Natl. Acad. Sci. USA 85(4): 1028-1032 (1988).

"Wildgoose, et al., Measurement of basal levels of factor VIIa in hemophilia A and B patients," Blood 80: 25-28 (1992).

Young, et al., "Triple helix formation inhibits transcription elongation in vitro," Proc. Natl. Acad. Sci. USA 88: 10023-10026 (1991).

Zamecnik, et al., "Inhibition of Rous sarcoma virus replication and cell transformation by a specific oligodeoxynucleotide," Proc. Natl. Acad. Sci. USA 75(1): 280-284 (1978).

Zamecnik, et al., "Inhibition of replication and expression of human T-cell lymphotropic virus type III in cultured cells by exogenous synthetic oligonucleotides complementary to viral RNA," Proc. Natl. Acad. Sci. 83(12): 4143-4146 (1986).

*Zhang, et al. "Intravenous somatic gene transfer with antisense tissue factor restores blood flow by reducing tumor necrosis factor-induced tissue factor expression and fibrin deposition in mouse meth-A sarcoma," J. Clin. Invest. 97(10):2213-2224 (1996).

*Zhang, et al. "Tissue factor controls the balance of angiogenic and antiangiogenic properties of tumor cells in mice," J. Clin. Invest. 94(3): 1320-1327 (1994).

Zhu, et al., "Systemic Gene Expression After Intravenous DNA Delivery into Adult Mice," Science 261: 209-211 (1993).

Zhu, et al., "Tissue factors on acute promyelocytic leukemia and endothelial cells are differently regulated by retinoic acid, arsenic trioxide and chemotherapeutic agents," Leukemia 13: 1062-1070 (1999).

Bogdanov, et al., "Alternatively spliced human tissue factor: a circulating, soluble, thrombogenic protein", *Nat Med.*, 9(4):458-62 (2003).

Giesen and Nemerson, "Tissue factor on the loose", *Semin Thromb Hemost*, 26(4):379-84 (2000).

Hatakeyama, et al., "Localization and activity of tissue factor in human aortic atherosclerotic lesions", *Atherosclerosis*, 133(2):213-9 (1997).

Van Der Logt, et al., "Alternative splicing is responsible for the presence of two tissue factor mRNA species in LPS stimulated human monocytes", *Thromb Haemost.*, 67(2):272-6 (1992).

* cited by examiner

FIG. 1

Membrane bound human tissue factor

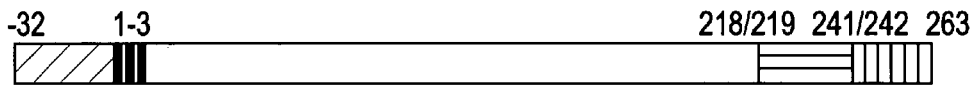

Alternatively spliced circulating human tissue factor

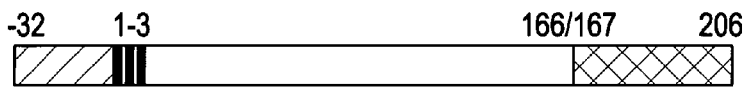

    Signal peptide for transport to cell surface, cleaved during post-translational processing to yield "mature" protein

    Staggered N-terminus resulting from cleavage of signal peptide at a site immediately before amino acid residues 1, 2, or 3.

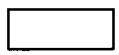    Extracellular region of the membrane bound human tissue factor

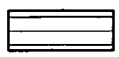    Transmembrane region of the membrane bound human tissue factor

    Intracellular region of the membrane bound human tissue factor

    C-terminal region unique to the alternatively spliced circulating human tissue factor TF activity for the fractions of human plasma centrifuged at 260,000×G alt-hTF activity Activity of relipidated alt-hTF with platelets and shear

SEQUENCE LISTING

```
<160> NUMBER OF SEQ ID NOS: 3

<210> SEQ ID NO 1
<211> LENGTH: 40
<212> TYPE: PRT
<213> ORGANISM: Homo sapiens

<400> SEQUENCE: 1

Tyr Ser Thr Ser Leu Glu Leu Trp Tyr Leu Trp Ser Ser Ser Leu Ser
1               5                   10                  15

Ser Ser Trp Leu Tyr Leu Tyr Thr Ser Val Glu Arg Gln Glu Trp Gly
            20                  25                  30

Arg Ala Gly Arg Arg Thr Pro His
        35                  40

<210> SEQ ID NO 2
<211> LENGTH: 123
<212> TYPE: DNA
<213> ORGANISM: Homo sapiens

<400> SEQUENCE: 2
tattctacat cattggagct gtggtatttg tggtcatcat ccttgtcatc atcctggcta      60
tatctctaca caagtgtaga aaggcaggag tggggcagag ctggaaggag aactccccac    120
tga                                                                  123

<210> SEQ ID NO 3
<211> LENGTH: 24
<212> TYPE: DNA
<213> ORGANISM: Homo sapiens

<400> SEQUENCE: 3
tcaggaaaga aatattctsg kkys                                            24
```

ALTERNATIVELY SPLICED CIRCULATING TISSUE FACTOR

CROSS-REFERENCE TO RELATED APPLICATIONS

This application claims the benefit of U.S. Provisional Application No. 60/316,244 filed on Aug. 30, 2001 by Yale Nemerson and Vladimir Bogdanov.

BACKGROUND OF THE INVENTION

The present invention is generally in the field of diagnostic and therapeutic reagents, and especially relates to a naturally occurring, circulating soluble alternatively spliced form of human tissue factor (alt-hTF) implicated in thrombotic conditions.

Tissue factor (TF) is the primary initiator of blood coagulation. At sites of vascular injury, formation of a TF:FVIIa complex leads to the generation of FXa, thrombin and the deposition of fibrin to limit hemorrhage. In contrast to its beneficial role in hemostasis, TF initiates life-threatening intravascular thrombosis in sepsis, atherosclerosis and cancer. More recently, TF has been proposed to play a role in other biological processes, including tumor-associated angiogenesis, metastasis and inflammation.

In combination with phospholipid vesicles, TF is used commercially in diagnostic clotting assays. It has always been thought that TF is present in only very small amounts on the surface of cells in the body and not in a circulating form. Before a recombinant source was available, laboratories used thromboplastin, an extract of human brain, placenta or rabbit brain and lung that was previously acetone extracted. The material was lyophilized and resuspended in buffered saline. Until cloned, the structure, exact molecular weight, role of carbohydrate, and relationship with other proteins in humans and other species were not known. Once cloned, the structure could be determined and large amounts of the membrane bound form of human tissue factor (263 amino acids in length; GenBank accession number J02931) or human tissue factor modified to yield a truncated or soluble tissue factor (between 218 and 243 amino acids in length) could be expressed in bacteria and mammalian cells. This tissue factor is used in commercial clotting assays. The soluble tissue factor has the advantage that it is easier to produce, purify and resuspend, as compared to the membrane bound form.

A shorter form of human tissue factor, consisting of amino acid residues 2–219 (Morrissey et al., Blood 1993; 81: 734–744) or 1–218 (Wildgoose et al., Blood 1992; 80: 25–28), produced by recombinant techniques and expression in bacteria, has been reported to be useful in an assay distinguishing between clotting factor VII and activated factor VIIa, when measured in the presence of high quantities of phospholipid.

In blood vessels of healthy humans, tissue factor is found primarily in the adventitia and thus physically separated from coagulation factors, which mainly circulate in an inactive form. Following injury, TF is exposed to blood and initiates the coagulation cascade. The resulting fibrin formation is essential for the initial repair of vessel damage to minimize blood-loss. Therefore, TF may be considered to form a hemostatic sheath around blood vessels essential for hemostasis and appears to be essential for life inasmuch as no TF deficiency has been reported and TF knockout mice do not survive beyond the perinatal period.

TF also plays a crucial role in pathological situations such as coronary artery disease or deep vein thrombosis (DVT). In the former, atherosclerosis is the underlying process leading to pathological disturbances of the arterial wall. The mechanism of venous thrombosis is poorly understood but perhaps blood-borne TF is involved, as reported by Giesen et al., Proc. Natl. Acad. Sci. USA 1999; 96: 2311–2315. Atheromae contain TF as judged by direct bioassay of excised lesions and by immunohistochemistry. Monocytes/macrophages are generally believed to be the major source of this TF although smooth muscle cells near experimental arterial injury contain TF. Upon plaque rupture, TF is exposed to flowing blood thereby allowing circulating factor VII/VIIa to complex with TF. This complex is the catalyst that initiates blood coagulation and thrombosis. However, the deposition of platelets on a TF-coated disc has been reported to inhibit this surface-bound TF, thus implicating circulating TF as necessary for thrombus propagation (Hathcock and Nemerson, Abstract OC2404, Thrombosis and Haemostasis, Supplement, 2001).

The etiology in deep vein thrombosis (DVT) is less well understood. One view of post-surgical thrombosis holds that the procedure causes exposure of TF and perhaps to its release into the blood stream. Combined with patient immobilization this could result in increased risk of thrombosis. Recently, the first clinical trial investigating the efficacy of inhibition of TF activity in prevention of DVT in post-orthopedic surgery patients, has given very promising results. In a open-label, phase II study, the nematode anti-coagulant protein NAPc2, which prevents activation of FX by binding to the TF:VIIa:X complex, resulted in a 50% reduction of DVT (Agnelli et al. Blood 2000;96: 491, abstract). This is the first clinical trial that confirms that TF activity plays a critical role in the mechanism of DVT.

It appears that soluble hTF may play a role in these disorders as well as normal coagulation, although its role is not clear. It is also not clear what form this protein may have, or its source. Previously reported functional mutants of human tissue factor have been truncation mutants, typically 1, 2, or 3–218/219, or mutants engineered to contain amino acid substitutions. One commercially available diagnostic reagent is truncated at residue 243.

It is therefore an object of the present invention to provide a method and reagents for diagnosis and treatment of thrombotic conditions based on TF.

It is a further object of the present invention to provide antibodies and other reagents for the detection of naturally occurring circulating soluble hTF.

It is a still further object of the present invention to provide reagents based on the discovery of a circulating soluble alt-hTF, for use as a diagnostic or pharmaceutical.

SUMMARY OF THE INVENTION

A previously unknown circulating form of soluble human tissue factor has been identified. This form of human tissue factor appears to be the result of alternative splicing and is therefore referred to as "alt-hTF." alt-hTF mRNA was detected in a cell line, HL-60. The cDNA region encoding the entire open reading frame of alt-hTF was cloned. The sequence encoding the alt-hTF mature peptide was expressed in bacteria. Alt-hTF consists of the first 166 amino acids of membrane bound TF, and a 40 amino acid C-terminal region unique to alt-hTF.

Alt-hTF is used as a diagnostic and is also a target for compounds to inhibit clotting and to treat disorders associated with elevated TF. It is also useful as a target for antibodies selectively reactive with alt-hTF, to remove it from the circulation for treatment of clotting or other disorders associated with elevated or abnormal levels of TF, including thrombotic conditions, cardiovascular disorders, DVT, DIC, and possibly metastatic cancers.

BRIEF DESCRIPTION OF THE DRAWINGS

FIG. 1 is a schematic of the full-length human tissue factor protein, the alternatively spliced human tissue factor protein, and the regions therein.

DETAILED DESCRIPTION OF THE INVENTION

I. Tissue Factor Compositions

Figure 2:
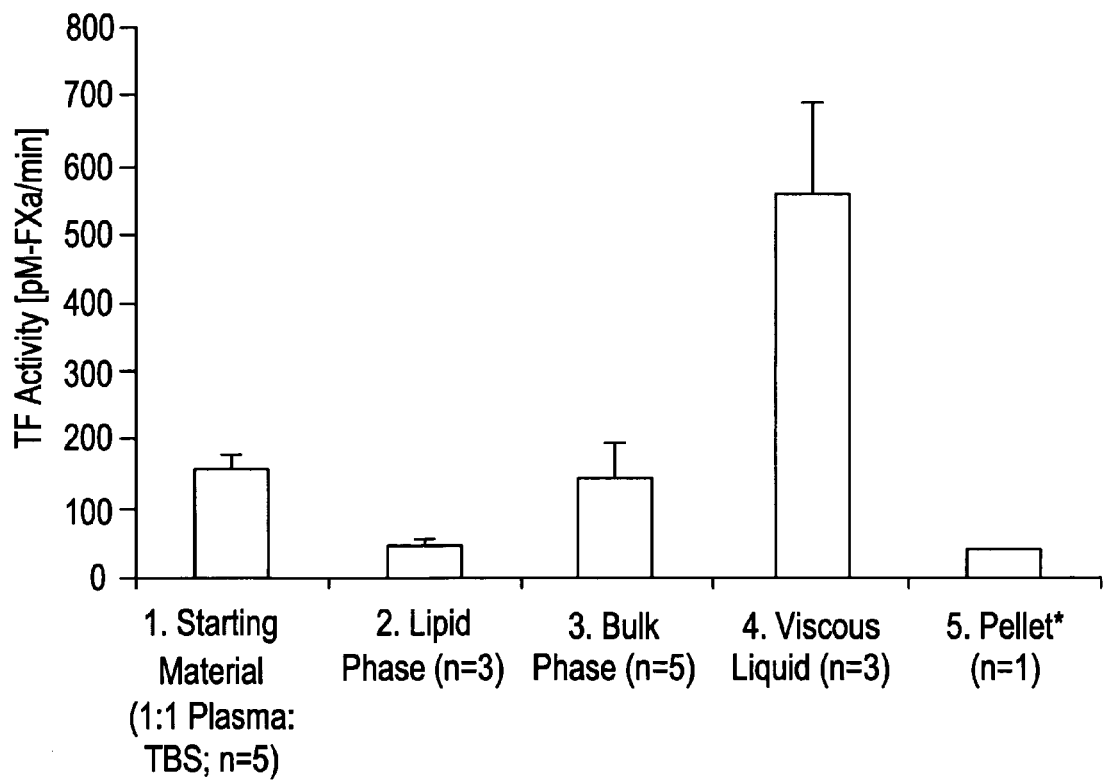
FIG. 2 is a graph of the TF activity [pM factor Xa/min] for the fractions of human plasma centrifuged at 260,000×G, i.e. starting material (1:1 plasma:TBS), lipid phase (n=3), bulk phase (n=5), viscous liquid (n=3), and pellet (n=1). Tissue factor was captured using immobilized antibodies to TF and then relipidated with 30:70 mixture of phosphatidyl serine and phosphatidyl choline. TF activity was measured by adding calcium (5 mM), clotting factors VIIa (1 nM) and X (150 nM), and measuring the subsequent rate of factor Xa generation.

Membrane bound human tissue factor ("TF") is a polymer of 263 amino acids. At one end of the polymer is an amino ("$NH_2$") group commonly referred to in the art as the amino (or "N")-terminus. At the other end of the polymer is a carboxyl ("COOH") group commonly referred to in the art as the carboxyl (or "C")-terminus. The region between the N- and C-termini is commonly referred to as the "internal" region. The schematic structure of the TF internal region is shown in FIG. 1. Truncated soluble versions of membrane bound TF are typically from 1–3 (i.e., amino acids 1, 2 or 3) to 218–219, although a truncated version may include additional residues of the transmembrane region from 219–241.

Similar to cytokine receptors, the extracellular domain of TF is composed of two fibronectin type III domains, both of which contribute to binding of coagulation factor VIIa. All four VIIa structural domains (alpha-carboxyglutamic acid (Gla), EGF1, EGF2 and protease) make TF contacts and, therefore, the total TF-VIIa intermolecular contact area is large (1800 Å$^2$). The dimensions of the entire TF:VIIa complex are about 115 Å in length and 40–50 Å in diameter. Most of the molecular interactions seen in the TF:VIIa crystal structure are in agreement with mutational and biochemical analysis of TF:VIIa and with binding residues identified from natural VII mutants, such as Arg 79 in the VIIa-EGF1 domain. The contacts provided by the VIIa light chain, particularly the EGF1 domain, are the main contributors to the binding energy (approximately 6.6–9.6 kcal/mol) and also to the contact area (1340 Å$^2$ of a total of 1810 Å$^2$). The contacts made by the VIIa protease domain are less important with respect to energetic contribution (2.3–3.1 kcal/mol), but have a critical role in transmitting allosteric changes within the VII protease domain leading to enhanced catalytic activity. The contact residues are mainly located on two adjacent alpha-helical stretches in the VIIa protease domain: VIIa Arg 134 (chymotrypsinogen numbering scheme used throughout) contacts TF-Asp 44 and TF-Trp 45, and VIIa-Met 164 of the adjacent alpha-helix contacts TF-Phe 76 and TF-Tyr 94.

In complex with TF, the VIIa active site is located about 80 Å above the membrane surface. Factors VII, IX, X, protein C and prothrombin are anchored to the phospholipid surface via their Gla domains, which contains several $Ca^{2+}$-binding sites. The VIIa-Gla domain has three hydrophobic residues at positions 4, 5 and 8 (Phe 4, Leu 5, Leu 8). Studies with coagulation factors IX, X and protein C suggest that occupancy of the $Ca^{2+}$-binding sites induces the surface exposure of these residues (in IX the residues are at position 6, 9 and 10) which then engage in hydrophobic interactions with the phospholipid layer. Indeed, as seen in the crystal structure of TF:VIIa the side chains of these three conserved hydrophobic residues point away from the rest of the Gla domain in a direction approximately perpendicular to the string of 6 calcium ions. Therefore, in analogy to the proposed function of the homologous residues in other coagulation enzymes, these amino acids may anchor VIIa to membranes by insertion into the outer phospholipid layer.

Mutational changes at TF residues Lys 165 and Lys 166 revealed another region of TF that is important for enzymatic activity of the TF:VIIa complex. These two lysine residues are part of a surface region that interacts with substrates and is located outside the TF-VIIa interface area. The main region is composed of 7 residues (Tyr 157, Lys 159, Ser 163, Gly 164, Lys 165, Lys 166 and Tyr 185) forming a continuous surface patch of about 500 Å$^2$. This substrate recognition region, which may further extend to the VIIa-Gla domain, contacts the Gla domains of substrates X and IX. It may also interact with the EGF-1 domain of substrates as suggested by the impaired activation of two naturally occurring IX-EGF1 domain variants, Gly48Arg and Gly48Val, and by IX-EGF1 domain swap experiments. This TF-substrate contact site may serve to properly align X and IX with respect to TF:VIIa complex allowing the formation of productive ternary TF:VIIa:substrate complexes. In agreement with the assigned functional importance of this TF region, anti-TF antibodies that bind to this region potently inhibit activation of substrates X and IX.

Another important interaction site with substrate is located in the VIIa protease domain centered around the inserted N-terminus. This exosite extends to the area of the $Ca^{2+}$-loop, a region that is topologically similar to the fibrinogen-binding exosite of thrombin. The crystal structure of the E76-peptide:VIIa complex reveals that the peptide binds near the $Ca^{2+}$-loop and thus only occupies a portion of the identified macromolecular substrate exosite on VIIa. In the context of an extended substrate recognition region that also includes the catalytic cleft region and the membrane-proximal TF domain, some steric interference with the protease exosite may be of little consequence to the overall binding affinity of X to TF:VIIa.

The TF-mediated enhancement of VIIa proteolytic activity is the aggregate of TF's interaction with substrate, the immobilization of VIIa onto the cell surface and the proper positioning of the VIIa protease domain. In addition, TF also induces allosteric effects at the VIIa catalytic center that contribute to an increase in VIIa enzymatic activity.

The overall conformation of the S1 recognition pocket as well as the position of the catalytic triad residues (His 57, Asp 102, Ser 195) in VIIa is very similar to other serine proteases, such as IXa and Xa. The Xa inhibitor, DX-9065a, which selectively binds to the Xa active site, demonstrates that differences in the S2–S4 region can be exploited to design enzyme-specific reversible inhibitors. The binding of VII to TF and its subsequent conversion to VIIa is believed to constitute the initial proteolytic process in coagulation.

As described herein, a new form of human tissue factor has been discovered. This form of human tissue factor circulates in plasma. Sequence analysis indicates that it is a soluble form of human tissue factor and apparently results from alternative splicing of the primary RNA transcript.

SEQ ID NO:1 is the carboxyl-terminus of naturally occurring circulating alternatively spliced human tissue factor, amino acid residues 167 to 206, referred to herein as "alt-hTF." This 40 amino acid sequence is unique to alt-hTF.

Y S T S L E L W Y L W S S S L S S S W L Y L Y T S V E R Q E W G R A G R R T P H (SEQ ID NO:1)

In one embodiment, a tissue factor protein comprises the sequence serine-serine-serine-leucine-serine-serine-serine (SEQ ID NO: 4), which is part of the 40 amino acid sequence unique to alt-hTF (SEQ ID NO: 1). The protein may have a high dielectric constant, containing outward pointing serine residues. Alternatively, the protein may have a low dielectric constant, containing inward pointing serine residues.

SEQ ID NO:2 is the cDNA sequence encoding amino acid residues 167 to 206 of alt-hTF. The stop codon is underlined.

tat tct aca tca ttg gag ctg tgg tat ttg tgg tca tca tcc ttg tca tca tcc tgg cta tat ctc tac aca agt gta gaa agg cag gag tgg ggc aga gct gga agg aga act ccc cac tga II. Screening of Patient Samples for Expression of alt-hTF SEQ ID NO:1 and SEQ ID NO:2 are useful in screening of patient samples for the presence of the normal alt-hTF protein, using hybridization assays of patient samples, including blood and tissues, as well as using the methods and reagents described in the examples. Screening can also be accomplished using antibodies, typically labeled with a fluorescent, radioactive, or enzymatic label, or by isolation of target cells and screening for clotting activity, as described in the examples. Typically, one would screen for expression on either a qualitative or quantitative basis, and for expression of functional alt-hTF.

Hybridization Probes

Reaction conditions for hybridization of an oligonucleotide probe or primer to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double-stranded DNA. Higher specificity is generally achieved by employing incubation conditions having higher temperatures, in other words more stringent conditions. In general, the longer the sequence or higher the G and C content, the higher the temperature and/or salt concentration required. Chapter 11 of the well-known laboratory manual of Sambrook et al., MOLECULAR CLONING: A LABORATORY MANUAL, second edition, Cold Spring Harbor Laboratory Press, New York (1990) (which is incorporated by reference herein), describes hybridization conditions for oligonucleotide probes and primers in great detail, including a description of the factors involved and the level of stringency necessary to guarantee hybridization with specificity.

The preferred size of a hybridization probe is from 10 nucleotides to 100,000 nucleotides in length. Below 10 nucleotides, hybridized systems are not stable and will begin to denature above 20° C. Above 100,000 nucleotides, one finds that hybridization (renaturation) becomes a much slower and incomplete process, as described in greater detail in the text MOLECULAR GENETICS, Stent, G. S. and R. Calender, pp. 213–219 (1971). Ideally, the probe should be from 20 to 10,000 nucleotides. Smaller nucleotide sequences (20–100) lend themselves to production by automated organic synthetic techniques. Sequences from 100–10,000 nucleotides can be obtained from appropriate restriction endonuclease treatments. The labeling of the smaller probes with the relatively bulky chemiluminescent moieties may in some cases interfere with the hybridization process.

Antibodies for Diagnostic or Therapeutic Use

Antibodies to alt-hTF can also be generated that are useful in detection, characterization or isolation of alt-hTF, as well as for modifying alt-hTF protein activity, in most cases, through inhibition of clotting. Antibodies are generated by standard techniques, using alt-hTF. Since the proteins exhibit high evolutionary conservation, it may be advantageous to generate antibodies to the protein of a different species of origin than the species in which the antibodies are to be tested or utilized, looking for those antibodies that are immunoreactive with the most evolutionarily conserved regions. Antibodies are typically generated by immunization of an animal using an adjuvant such as Freund's adjuvant in combination with an immunogenic amount of the protein administered over a period of weeks in two to three week intervals, then isolated from the serum, or used to make hybridomas that express the antibodies in culture. Because the methods for immunizing animals yield antibody that is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarity-determining hypervariable regions (CDRs) are of non-human origin, whereas all framework regions (FR) of variable domains are products of human genes. These "humanized" antibodies present a lesser xenographic rejection stimulus when introduced to a human recipient.

To accomplish humanization of a selected mouse monoclonal antibody, the CDR grafting method described by Daugherty, et al., 1991 *Nucl. Acids Res.,* 19:2471–2476, incorporated herein by reference, may be used. Briefly, the variable region DNA of a selected animal recombinant anti-idiotypic ScFv is sequenced by the method of Clackson, T., et al., 1991 *Nature,* 352:624–688, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) that incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA that codes for a flexible peptide. This assembly generates a single-chain Fv fragment (ScFv) that incorporates the complete antigen-binding domain of the antibody. Compared to the intact monoclonal antibody, the recombinant ScFv includes a considerably lower number of epitopes, and thereby presents a much weaker immunogenic stimulus when injected into humans.

The antibodies can be formulated in standard pharmaceutical carriers for administration to patients in need thereof. These include saline, phosphate buffered saline, and other aqueous carriers, and liposomes, polymeric microspheres and other controlled release delivery devices, as are well known in the art. The antibodies can also be administered with adjuvant, such as muramyl dipeptide or other materials approved for use in humans (Freund's adjuvant can be used for administration of antibody to animals). Antibodies can also be immobilized as discussed below.

Methods for Detection and Measurement of Circulating alt-hTF

As described in the examples, the levels of alt-hTF can be measured in plasma using a simple antibody immunoassay, or the mRNA can be measured using standard RT-PCR or other nucleotide based diagnostic assays.

In a preferred embodiment for clinical use, one would utilize an antibody that differentiates between native membrane bound TF or a truncated form thereof, and the alt-hTF. This can be obtained by immunizing with the alt-hTF, alone or conjugated to a carrier, with or without adjuvant, then removing antibody that is produced that binds to the membrane bound TF using for example a column having membrane bound TF immobilized thereon. In a preferred embodiment, a fragment of the alt-hTF derived from the last forty amino acids of the protein, is used for immunization to generate alt-hTF antibodies.

It is expected that levels of alt-hTF will vary with condition and disorder. Accordingly, conditions such as predisposition to clot will be predictable based on the levels of alt-hTF in the plasma. Normal levels are in the picomolar range. It is expected that the levels will be elevated in individuals having thrombotic disorders such as DVT.

III. Therapeutic Methods Targeting alt-hTF

It is well established that TF is a membrane-anchored cell-surface protein that initiates coagulation when blood contacts damaged tissue. However, in the process of thrombus growth, membrane bound TF is rapidly covered by several layers of adherent platelets and fibrin and thus is physically separated from the site of vascular injury. Recently, the role of blood-borne TF in thrombogenesis has been emphasized. In a rabbit venous thrombosis model, a specific anti-TF antibody inhibited thrombus formation. In this model, a collagen-coated cotton thread is inserted into the jugular vein and thrombus growth on the cotton-thread is monitored by measurement of the incorporated radioactive fibrinogen. Since no obvious vessel damage is involved in this model, it was concluded that the observed antithrombotic effect is due to inhibition of TF that is circulating in the blood. In parallel experiments, ex vivo perfusion of human blood over isolated pig aortic media and over collagen coated glass slides resulted in thrombi that stained for TF antigen. Inhibition of TF by a factor VIIa inhibitor reduced thrombus formation on the collagen coated slides. Furthermore, light- and electron-microscopic analysis of ex vivo human thrombi demonstrated TF staining of platelet surface, fibrin structures, monocytes and granulocytes. Because the samples were fixed with paraformaldehyde within five minutes, de novo synthesis of monocyte and granulocyte associated TF can be ruled out. Therefore, these experiments demonstrate the thrombogenic potential of blood-borne TF.

In a dog thrombosis model, granulocytes were associated with thrombi in damaged jugular veins and were shown to be the source of thrombus associated TF activity.

Elevated levels of shed membrane vesicles with procoagulant potential were detected in patients with acute coronary syndromes (Mallat, et al., Circulation 2000;101: 841–843; Kim, et al. Cardiology 2000;93: 31–36). Furthermore, procoagulant microparticles have been reported to be elevated in patients suffering meningococcal sepsis and patients with lupus anticoagulant (Nieuwland, et al., Blood 2000; 95; Combes, et al., J. Clin. Invest. 1999;104: 93–102). It is possible that circulating neutrophils might capture these vesicles and thereby serve as a carrier that provides the adhesion molecules necessary for recruitment of TF to growing thrombi.

A series of human studies also suggest that blood-borne TF might be an important factor in the etiology of several diseases. These studies involved TF associated with microparticles and are therefore assumed to reflect the activity of full-length TF in cell-generated particles. Giesen et al. (*Proc. Natl. Acad. Sci. USA,* 1999; 96:2311–2315) added detergent and phospholipids to antibody-captured material. Accordingly, it is uncertain whether the measured TF activity was particle-bound in the circulation.

Plasma TF levels were quantified by ELISA and reported to be increased in patients with unstable angina (Lee, et al., Exp. Mol. Med. 1999;31: 159–164) myocardial infarction (Soejima, et al., J. Am. Coll Cardiol 1999;34: 983–988) trauma- and septic-patients (Gando, et al., Thromb Haemost 1998;79: 1111–1115), patients with disseminated intravascular coagulation (Shimura, et al., Amer. J. Hematol. 1997; 55: 169–174), antiphospholipid syndrome (Atsumi, et al., Thromb. Haem. 1997;77: 222–223) and sickle cell disease (Key, et al., Blood 1998;91: 4216–4223). Interestingly, several clinical studies designed to investigate the risk factors for coronary artery disease reported that the incidence of myocardial infarction rises with increasing leukocyte number (Lowe, et al., Thromb. Haem. 1985;54: 700–703; Corre, et al., The Lancet 1971; Sep. 18: 632–634; Friedman, et al., N. Engl. J. Med. 1974;290: 1275–1278; Matetzky, et al., Circulation 2000;102: 602–604). Furthermore, levels of blood-borne TF were reported to correlate with the severity of the coronary artery disease state (Lee, et al., 1999; Leatham, et al., Br Heart J. 1995;73: 10–3; Misumi, et al., Am. J. Cardiol 1998;81: 22–6; Moreno, et al., Circulation 1996;94: 3090–3097; Belch Blood Coag. Fibrinolysis 1990;1: 183–192; Suefuji, et al., Am Heart J. 1997; 134: 253–259; Soejima, et al., Circulation 1999;99: 2908–2913; Bach, et al., Biochemistry 1986;25: 4007–4020). Thus, clinical studies have established the correlation of TF with disease progression.

The association of TF with malignancy has been recognized for many years and TF expression levels have been correlated with the invasive and metastatic potential of many types of malignancies (for reviews, see Pendurthi, et al., J Biol Chem 2000;275: 14632–41; Oemar, et al., Circulation 1997;95: 831–9; Camerer, et al., J. Biol. Chem. 2000;275: 6580–5; Dvorak, et al., Cancer Metastasis Rev 1983;2: 41–73; Fidler Cancer Res 1978;38: 2651–60). Early ideas about this correlation were focused on the TF-dependent initiation of proteolytic events leading to the formation of a fibrin coat on the surface of malignant cells that had entered the bloodstream after detachment from a primary tumor (Rickles and Edwards. Blood 1983;62: 14–31). This fibrin coat was thought to protect the circulating tumor cells from immune surveillance until they could adhere to the endothelium of a capillary bed and then become established as metastatic lesions (Hu, et al., Oncol. Res. 1994;6: 321–7). The correlation between metastatic potential and TF expression was brought into sharper focus when Mueller et al. (Murray Br J Cancer 1991;64: 422–4) showed that highly metastatic human melanoma cells expressed levels of TF that were 1000 times higher than non-metastatic melanoma cells. The metastatic potential of the high TF expressing melanoma cell lines could be eliminated by incubation with an inhibitory monoclonal anti-TF antibody whereas incubation with a non-inhibitory monoclonal anti-TF antibody did not reduce the incidence of metastasis. These authors concluded that the procoagulant function of TF was essential for metastasis and that a downstream component of the coagulation cascade was responsible for the establishment of metastatic lesions. As work in this area progressed, reports began to emerge that linked TF to elevated levels of Vascular Endothelial Growth Factor (VEGF) and tumor angiogenesis (Abdulkadir et al. Hum Pathol 2000 31:443–447; Takano et al. Br J Cancer 2000 82:1967–1973).

In Clauss, et al., J. Exp. Med. 1990;172: 1535–45, a connection between TF levels, upregulation of VEGF, angiogenesis and tumor growth was demonstrated by transfection of a murine fibrosarcoma cell line (Meth-A) with mouse TF cDNA. The TF cDNA-transfected Meth-A sarcoma cell lines grew more rapidly than controls. The resulting tumors were more highly vascularized and produced increased amounts of VEGF mRNA compared to control cells that had been transfected with the same vector lacking the TF cDNA insert. These authors also reported that tumor cell mediated angiogenesis was independent of thrombin since hirudin did not inhibit the growth of endothelial cells treated with tumor cell supernatants. Zhang, et al. (J Clin Invest 1996 97:2213–2224) also used transfection with antisense TF cDNA to show that the effect of TF on tumor cell growth could be reversed. In addition to these results and others they concluded that mechanisms apart from procoagulant activity were important for TF mediated tumor growth. Thus, the fibrin coat on the tumor cell surface was deemed not to be an adequate explanation for the effect of TF on tumor cell growth and metastasis. Following this, Fischer, et al. (Folkman. N Engl J Med 1995;333: 1757–63) demonstrated that a high level TF producing human melanoma cell line (M24 met) generated thrombin that contributed to the establishment of metastatic lesions via signaling through a thrombin receptor that was present on these cells. To verify this, they showed that the thrombin receptor was activated by the thrombin receptor peptide agonist TRAP-14, which generated proliferative signals and increased intracellular $Ca^{++}$ levels.

Zhang, et al., J. Clin. Invest. 1994;94: 1320–7 have investigated human pancreatic cell lines that either overexpress TF or fail to express TF at detectable levels. After treatment of these cell lines with VIIa, expression of the urokinase receptor (u-PAR) was upregulated only in a pancreatic cell line SW979 that had high TF levels. u-PAR expression was increased in a dose dependent manner, but not with their MIA-PAC2 cell line that had low levels of TF. The increase in u-PAR expression was also correlated with tumor cell invasion in vitro. Functionally inactivated VIIa (VIIai) failed to upregulate u-PAR expression in SW979 cells, indicating that the proteolytic activity of VIIa was vital for this response. These authors also found that treatment of SW979 cells with Xa did not upregulate expression of the u-PAR gene and they suggest that the TF-VIIa complex itself, rather than TF-initiated thrombin generation, is responsible for this effect. This mechanism differs from the one proposed by Fischer, et al., where downstream substrates of the TF-VIIa complex, which include Xa and thrombin, were deemed to be essential.

To summarize, the TF-VIIa complex initiates coagulation and intracellular signaling. It also alters gene expression and promotes metastasis in murine models. Various mechanisms, all involving active VIIa, have been proposed to account for these varied responses. Accordingly, one should be able to treat clotting or the disorders discussed above, by blocking the activity, or removal of, the alt-hTF, using standard techniques to obtain suitable antibodies or other compounds specific for the alt-hTF, or removal techniques such as a column or filter having immobilized therein on antibody specifically immunoreactive with the alt-hTF.

IV. Designing or Screening for Drugs Modifying or Altering the Extent of alt-hTF Function or Expression alt-hTF is useful as a target for compounds that turn on, or off, or otherwise regulate clotting or other disease processes mediated by alt-hTF. The assays described in the examples clearly provide routine methodology by which a compound can be tested. The in vitro studies of compounds that appear to inhibit alt-hTF are then confirmed by animal testing.

A number of animal models are useful and predictive of efficacy in humans. For example, as reviewed by Leadley, et al. J Pharmacol Toxicol Methods 2000 March–April;43(2): 101–16, over the past two decades, great advances have been made in the pharmacological treatment and prevention of thrombotic disorders (e.g., tissue plasminogen activators, platelet GPIIb/IIIa antagonists, ADP antagonists such as clopidogrel, low-molecular weight heparins, and direct thrombin inhibitors). New research is leading to the next generation of antithrombotic compounds such as direct coagulation FVIIa inhibitors, tissue factor pathway inhibitors, gene therapy, and orally active direct thrombin inhibitors and coagulation Factor Xa (FXa) inhibitors. Animal models of thrombosis have played a crucial role in discovering and validating novel drug targets, selecting new agents for clinical evaluation, and providing dosing and safety information for clinical trials. In addition, these models have provided valuable information regarding the mechanisms of these new agents and the interactions between antithrombotic agents that work by different mechanisms. Genetic models have also been used in thrombosis/hemostasis research and pharmacology, for example, gene-therapy for hemophilia, is an example of how animal models have aided in the development of the therapies that are now being evaluated clinically.

Studies Based on Inhibition of Clotting are Predictive for Indirect Effects of Alteration of alt-hTF Binding Assays for testing compounds for useful activity can be based solely on interaction with the alt-hTF protein. Alternatively, the assays can be based on interaction with the gene sequence encoding the alt-hTF protein, or the regulatory sequences directing expression of the alt-hTF protein. For example, antisense that binds to the regulatory sequences, and/or to the protein encoding sequences can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothiodates and methylation), then screened initially for alteration of alt-hTF activity in transfected or naturally occurring cells which express alt-hTF, then in vivo in laboratory animals. Typically, the antisense would inhibit expression. However, sequences which block those sequences which "turn off" synthesis can also be targeted.

The alt-hTF protein for study can be isolated from either naturally occurring cells or cells which have been genetically engineered to express the alt-hTF protein, as described in the examples above.

Drug Design Using Computational Chemistry and Molecular Modeling

Medicinal chemistry is an interdisciplinary approach used to design small molecules, such as organic chemicals or peptides, for use as therapeutic agents. Medicinal chemists use a variety of technology platforms to discover and design drugs. These include combinatorial chemistry, computational chemistry, molecular modeling, high-throughput screening (HTS), enzymology, and pharmacology. The goal is to identify portions of a molecule responsible for particular activities, such as receptor binding or protein interaction. These properties can then be exploited to rationally design more effective drugs. Based on the structure and properties of a lead drug candidate, combinatorial chemists synthesize a series of closely related analogs. Computational chemistry tools are then used to simulate the interactions of structural elements with macro-molecules, such as receptors, in order to correlate structure with activity. Scientists need to be able to predict function based upon structural elements. Computational chemistry tools include tools for 3-D structure analysis, quantitative structure-activity relationship analysis, and comparative molecular field analysis, among others. Several companies market software and services to help speed drug discovery and lead optimization programs. For example, Tripos Inc., St. Louis, produces a variety of "chemically intelligent" modeling and analysis tools through its discovery software program. Bio Balance, New York, is an example of a company that does computer modeling of proteins for drug design.

Computer Assisted Drug Design

Molecular modeling applications use falls into two broad categories: interactive visualization and computational analyses. The latter involves objective, computational analysis and is based upon known biophysical features of the molecule and established mathematical concepts that describe those features. These two approaches to modeling can be used alone or collectively to computationally derive a structure. Furthermore, these tools also can be used to reconstruct best-fit models from known structures when researchers make theoretical substitutions, insertions, or deletions in the composition of the macromolecule. Three of the most prominent uses of modern molecular modeling applications are structure analysis, homology modeling, and docking. Structure analysis centers on computational visualization of a molecule, provided its 3-D atomic coordinates have been elucidated, usually by X-ray crystallography or nuclear magnetic resonance (NMR). This information usually resides in major, world-accessible databases including the Brookhaven Protein Data Bank for protein structures, the Nucleic Acids DataBase at Rutgers University for DNA structures, and the Cambridge Crystallographic Data Centre (CCDC) for small molecule (nonprotein/DNA/RNA) structures. Using structure analysis tools, investigators may dissect the intricate features of a molecule's structure or examine potential structural changes due to changes in the atomic or molecular composition of the molecule or macromolecule. Three-dimensional structural analyses give the researcher the ability to examine the spatial, electrostatic, hydrophilic/hydrophobic, potential bonding, or the relationships of the substitute residue with neighboring residues on the same or separate chains. Homology modeling has been very important these last few years, as researchers in academia and the pharmaceutical industry seek model structures for proteins whose crystal structures have not yet been solved. Homology modeling is also referred to as "comparative modeling" and "knowledge-based modeling." It is essentially the theoretical creation of a structure using structural elements borrowed from another protein within the same protein family (usually based on primary sequence and/or secondary structure features) whose crystal structure is known. The process involves alignment of the two sequences, usually performed by any of a number of bioinformatics tools. The result of this alignment is then fed into a homology modeling application, which uses the known crystal structure and the alignment to construct a "draft" (preliminary) structure for the "structureless" protein. This structure is then refined: loops are constructed (for "gapped" alignment regions), the residue side chain spatial placement is modified, and the entire "draft" homology structure is fine-tuned. A number of commercial and academic software packages perform homology modeling. Among the most widely used are INSIGHT II/HOMOLOGY and Modeler (MSI), Look/GeneMine (MAG), and SYBYL/COMPOSER (Tripos).

Docking modeling is used to better understand and model novel protein-protein and protein-ligand interactions (that is, receptor and ligand binding). This provides an avenue to examine and model receptor sites and assess potential ligands (drugs) abd receptor-ligand associations. These techniques allow one to examine binding specificity and decipher the details of the atomic interactions involved in molecular recognition and catalysis. Some of the more widely used docking programs include AutoDock (Oxford Molecular Group), DOCK (Molecular Design Institute-UC San Francisco), FTDOCK (Biomolecular Modeling Laboratory), INSIGHT II (MSI), SYBYL/FLEXIDOCK (Tripos) and MidasPlus (Computer Graphics Laboratory, UC San Francisco). Important challenges in this area are optimizing the conformations of the ligand and receptor, and modeling the relevant non-bonded interactions between two species. The docking programs GOLD (CCDC) and Flex X (Tripos) take the approach of applying data from X-ray crystal structures in the Cambridge Structural Database that is a source of experimental information on non-bonded contacts. Many commercial applications such as Cerius$^2$, INSIGHT II (MSI), HyperChem (Hypercube), Look/GeneMine (MAG), SYBYL (Tripos)—provide transparent interfaces to these tools. Structural images created from X-ray and NMR coordinate files represent a snapshot in time for any given structure. In reality, the atoms and molecules are constantly moving as a result of thermal molecular motion and interactions with their environment. This interaction represents both passive and active processes (for example, interactions with nearby water molecules and substrate, respectively). In either case, these interactions translate into structural change for the macromolecule. The molecular dynamics approach to structure analysis seeks to understand and predict these structural changes based upon energy minimization. Dynamics analyses are based on an assessment (usually performed by molecular mechanics methods) of the free energy changes between two different structural states (a protein with and without bound ligand, for example). By mathematically extrapolating free energy changes, one can model a particular structure, which would have the appropriate calculated total free energy. These calculations can be reiterated for practically an infinite set of time points, thus allowing a researcher to model the temporal dynamics of macromolecule structure, for instance, as it performs some catalytic or binding function. Modeling programs that utilize molecular dynamics function include HyperChem (Hypercube), INSIGHT II/Discover (MSI), AMBER, CAChe (OMG), SYBYL (Tripos), Alchemy 2000 (Tripos), Spartan (Wavefunction). Molecular mechanics emphasizes the potential energy of the molecule as a function of its component atoms, bonds and their angles, and charges—in general, the entire macromolecular environment. This approach attempts to calculate an energy potential for the entire molecule. Structure assignment is based on the assumption that the structure with the lowest energy potential represents a best fit for the molecule's structure as it exists in nature. Modeling programs that utilize molecular mechanical methods include HyperChem (Hypercube), SCULPT (ISI), SYBYL (Tripos), INSIGHT II (MSI), AMBER, CAChe (OMG).

Quantum mechanics methods of "structure" determination are based upon the electronic makeup of a molecule. Electron distribution is defined by one of many quantum theories; the most widely known and used is the molecular orbital theory. This and other theories provide the basis for mathematically determining a number of physicochemical parameters (electric multipole moments of a molecule, electron density distribution, electron affinities, nuclear atomic charge, electrostatic potentials, heats of formation, ionization energies, etc.) that may be utilized to construct a model structure. Quantum mechanisms offer advantages over the other methods in that it can be used to examine molecules at various electronic ("energy") states or during chemical bond formation and breakage. In essence, quantum mechanical methods are better at predicting chemical reality. Modeling with quantum mechanical methods is best for detailed analyses of molecule surface electrostatics, and thus protein-protein interactions and active/binding site interpretations (structure-function relationships, mechanistics of catalysis and/or binding). Modeling programs that utilize quantum mechanical methods include Cerius$^2$, INSIGHT II (MSI), HyperChem (Hypercube), and SYBYL (Tripos). Many modeling applications make use of several mathematical methods; for example, Mac/PC/UNIX SPARTAN (Wavefunction), SYBYL (Tripos), and INSIGHT II (MSI) use a combination of molecular mechanics, quantum mechanical, and/or molecular dynamics methods. Multi-routine programs such as Cerius$^2$ (Tripos), INSIGHT II (MSI), Look/GeneMine (MAG), MidasPlus (Computer Graphics Lab), and SYBYL (Tripos) are especially important to researchers performing homology modeling and docking, where various kinds of computational routines are utilized in the model-building process. Such a process incorporates all physicochemical properties into the computational equation to derive the best thermodynamically stable structure, a structure that should depict a functional molecule.

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Although described above with reference to design and generation of compounds that could alter binding, one could also screen libraries of known compounds, including natural products or synthetic chemicals, and biologically active materials, including proteins, for compounds that are useful.

Generation of Nucleic Acid Regulators

Nucleic acid molecules containing the 5' regulatory sequences of the TF gene can be used to regulate or inhibit gene expression in vivo. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16). Furthermore, a number of viral and nonviral vectors have been developed that enable the introduction of nucleic acid sequences in vivo (see, e.g., Mulligan, 1993 *Science,* 260, 926–932; U.S. Pat. No. 4,980,286; U.S. Pat. No. 4,868,116; incorporated herein by reference). Delivery systems are available in which nucleic acid is encapsulated in cationic liposomes that can be injected intravenously into a mammal. This system has been used to introduce DNA into the cells of multiple tissues of adult mice, including endothelium and bone marrow (see, e.g., Zhu et al., 1993 *Science* 261, 209–211; incorporated herein by reference).

The 5' flanking sequences of the TF gene can also be used to inhibit the expression of alt-hTF. For example, an antisense RNA of all or a portion of the 5' flanking region of the TF gene can be used to inhibit expression of alt-hTF in vivo. Expression vectors (e.g., retroviral expression vectors) are available in the art that can be used to generate an antisense RNA of a selected DNA sequence that is expressed in a cell (see, e.g., U.S. Pat. No. 4,868,116; U.S. Pat. No. 4,980,286). Accordingly, DNA containing all or a portion of the sequence of the 5' flanking region of the TF gene can be inserted into an appropriate expression vector so that upon passage into the cell, the transcription of the inserted DNA yields an antisense RNA transcript that is complementary to the mRNA transcript of the alt-hTF protein normally found in the cell. This antisense RNA transcript of the inserted DNA can then base-pair with the normal mRNA transcript found in the cell and thereby prevent the mRNA from being translated. It is of course necessary to select sequences that are downstream from the transcriptional start sites for the TF gene to ensure that the antisense RNA contains sequences complementary to those present in the mRNA.

Antisense RNA can be also generated in vitro, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zamecnik et al., 1978 *Proc. Natl. Acad. Sci. USA* 75, 280–284; Zamecnik et al., 1986 *Proc. Natl. Acad. Sci.*, 83, 4143–4146; Wickstrom et al., 1988 *Proc. Natl. Acad. Sci. USA* 85, 1028–1032; Crooke, 1993 *FASEB J.* 7, 533–539.) Inhibition of expression of a gene by antisense oligonucleotides is also possible if the antisense oligonucleotides contain modified nucleotides (see, e.g., Offensperger et. al., 1993 *EMBO J.* 12, 1257–1262 (antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079–7083 (synthesis of antisense oligonucleoside phosphoramidates and phosphorothioates); Sarin et al., 1989 *Proc. Natl. Acad. Sci. USA* 85, 7448–7794 (synthesis of antisense methylphosphonate oligonucleotides); Shaw et al., 1991 *Nucleic Acids Res* 19, 747–750 (synthesis of 3' exonuclease-resistant oligonucleotides containing 3' terminal phosphoroamidate modifications); incorporated herein by reference).

Inhibition of expression of a gene can also be achieved by using small double-stranded RNA molecules (21–25 base pairs in length) by means of a process known as RNA interference (see, e.g., Sharp, *Genes & Development*, 2001, 15:485–490). Double-stranded RNA molecules can be synthesized in vitro and then introduced into living cells (see, e.g., Donze et al., 2002 *Nucleic Acid Research*, 30:e46) or synthesized from a DNA template that was stably incorporated into cells (see, e.g., Sui et al., 2002 *Proc. Natl. Acad. Sci. USA* 99:5515–5520). Double-stranded RNA molecules have been shown to inhibit HIV-1 infection (see Novina et al., 2002, Nature Medicine, 8:681–686) and expression of the full-length tissue factor (see Holen et al., Nucleic Acid Research 2002, 30:1757–1766). Thus, double-stranded RNA molecules containing the region unique to alt-hTF mRNA, i.e. the site of splicing of exon 4 to exon 6, may be used to selectively inhibit expression of alt-hTF protein in vivo.

The sequences of the 5' flanking region of the TF gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., 1989 Maher et al., *Science* 245, 725–730; Orson et al., 1991 *Nucl. Acids Res.* 19, 3435–3441; Postal et al., 1991 *Proc. Natl. Acad. Sci. USA* 88, 8227–8231; Cooney et al., 1988 *Science* 241, 456–459; Young et al., 1991 *Proc. Natl. Acad. Sci. USA* 88, 10023–10026; Duval-Valentin et al., 1992 *Proc. Natl. Acad. Sci. USA* 89, 504–508; 1992 Blume et al., *Nucl. Acids Res.* 20, 1777–1784; 1992 Grigoriev et al., *J. Biol. Chem.* 267, 3389–3395.) For example, oligonucleotides should generally be greater than 14 nucleotides in length to ensure target sequence specificity (see, e.g., Maher et al., 1989; Grigoriev et al., 1992). Also, many cells avidly take up oligonucleotides that are less than 50 nucleotides in length (see e.g., Orson et al., 1991; Holt et al., 1988 *Mol. Cell. Biol.* 8, 963–973; Wickstrom et al., 1988 *Proc. Natl. Acad. Sci. USA* 85, 1028–1032). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., 1989; Grigoriev et al., 1992).

Methods to produce or synthesize oligonucleotides are well known in the art and synthetic oligonucleotides are now commercially available. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., in *Ann. Rev. Biochem.* 1984 53, 323–356 (phosphotriester and phosphite-triester methods); Narang et al., in *Methods Enzymol.*, 65, 610–620, 1980 (phosphotriester method)). Accordingly, DNA sequences of the 5' flanking region of the TF gene described herein can be used to design and construct oligonucleotides including a DNA sequence consisting essentially of at least 15 consecutive nucleotides, with or without base modifications or intercalating agent derivatives, for use in forming triple helices specifically within the 5' flanking region of the TF gene in order to inhibit expression of the gene.

In some cases it may be advantageous to insert enhancers or multiple copies of the regulatory sequences into an expression system to facilitate screening of methods and reagents for manipulation of expression.

Random Generation of alt-hTF Encoding Sequence Binding Molecules

Molecules with a given function, catalytic or ligand-binding, can be selected for from a complex mixture of random molecules in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992).

Preparation of alt-hTF Protein Fragments

Compounds that are effective for blocking binding of the alt-hTF can also consist of fragments of the alt-hTF protein, expressed recombinantly and cleaved by enzymatic digest or expressed from a sequence encoding a peptide of less than the full length alt-hTF protein. These will typically be soluble proteins, i.e., not including the transmembrane and cytoplasmic regions, although smaller portions determined in the assays described above to inhibit or compete for binding to the alt-hTF protein can also be utilized. It is a routine matter to make appropriate alt-hTF protein fragments, test for binding, and then utilize them. The preferred fragments are of human origin, in order to minimize potential immunological response. The peptides can be as short as five to eight amino acids in length and are easily prepared by standard techniques. They can also be modified to increase in vivo half-life, by chemical modification of the amino acids or by attachment to a carrier molecule or inert substrate. Based on studies with other peptide fragments blocking alt-hTF binding, the $IC_{50}$, the dose of peptide required to inhibit binding by 50%, ranges from about 50 µM to about 300 µM, depending on the peptides. These ranges are well within the effective concentrations for the in vivo administration of peptides, based on comparison with the RGD-containing peptides, described, for example, in U.S. Pat. No. 4,792,525 to Ruoslaghti, et al., used in vivo to alter cell attachment and phagocytosis. The peptides can also be conjugated to a carrier protein such as keyhole limpet hemocyanin by its N-terminal cysteine by standard procedures such as the commercial Imject kit from Pierce Chemicals or expressed as a fusion protein, which may have increased efficacy. As noted above, the peptides can be prepared by proteolytic cleavage of the alt-hTF protein, or, preferably, by synthetic means. These methods are known to those skilled in the art. An example is the solid phase synthesis described by J. Merrifield, 1964 *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having the sequence identical to that of the alt-hTF described herein, or substitutions or additions of amino acids, which can be screened for activity as described above.

The peptide can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

V. Pharmaceutical Compositions

Peptides are generally active when administered parenterally in amounts above about 1 µg/kg of body weight. Based on extrapolation from other proteins, for treatment of most inflammatory disorders, the dosage range will be between 0.1 to 70 mg/kg of body weight. This dosage will be dependent, in part, on whether one or more peptides are administered. In the preferred embodiment, with regard to alt-hTF, the peptide sequences present in the C-terminal region of alt-hTF (amino acid residues 167–206) should be the most optimal. Because this sequence has not been described in other proteins, this would be a unique target to inhibit binding alt-hTF to platelets, thereby uniquely inhibiting the activity of alt-hTF.

Compounds that alter alt-hTF protein activity and/or binding (referred to generally herein as "binding activity") are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

VI. Removal of alt-hTF from Patients or Patient Samples

The antibodies to alt-hTF protein can be used to remove alt-hTF from patient blood, by immobilizing the alt-hTF antibodies on a suitable substrate, such as the cellulose membrane of a dialysis unit, using conventional coupling, for example, using carboimide. The patient's blood is then dialyzed through the unit.

The present invention will be further understood by reference to the following non-limiting examples.

EXAMPLE 1

Characterization of Tissue Factor Activity in Plasma

An acellular form of tissue factor that appears to circulate in human plasma in a latent form has been identified. Upon shear-induced binding to platelets, this protein exhibits enzymatic activity and, therefore, may serve as a potential trigger for initiating or propagating thrombosis. Following high-speed centrifugation of already platelet-poor plasma, the activity remained in the bulk aqueous phase indicating that blood-borne TF is soluble in an aqueous medium. In this regard, we note that alt-hTF is extracted from bacteria simply by osmotic shock.

Citrated blood was processed as follows. After centrifugation at 200×G for 15 minutes, the cell pellet was discarded and the supernatant was mixed 1:1 with Tris-buffered saline (TBS) and is referred to as the "starting material." Nine mL of the starting material was removed and centrifuged at 260,000×G for 4 hours. Following high-speed centrifugation, 4 distinct layers were evident and their volume fractions were estimated: an upper lipid phase (17% of volume), a bulk-aqueous phase (52%), a lower viscous phase (23%) and a pellet (3%). Samples from the starting material and each of the three upper phases were extracted and assayed for TF activity using a standardized protocol. In one experiment, the pellet was resuspended in 4.5 mL of TBS and also assayed for TF activity.

In the standardized assay for TF activity, 480 µL of a given sample is incubated with 20 µL of Triton X-100 for 1 hour, and then incubated overnight with 65 µL of agrose beads covalently linked to a rabbit anti-human TF antibody (0.5 mg antibody per mL of agarose). The beads were washed 5 times with hepes-buffered saline (HBS) and the bound antigen was eluted with 6M guanidine dissolved in HBS. The eluted protein was collected and incubated with phospholipids (30% phosphatidyl serine, 70% phosphatidyl choline; 75 µM total) and n-octyl-β-D-glucopyranoside. The samples were dialyzed to remove the detergent and allow the formation of lipid vesicles in the presence of the eluted protein. The dialyzed samples were supplemented with calcium (5 mM), coagulation factor VIIa (1 nM) and coagulation factor X (150 nM), and the rate of appearance of FXa was measured using a standard assay.

The results are shown in FIG. 2. The TF activity associated with the starting material was 158.5 pM-FXa/min. Following ultracentrifugation, TF activity measured in each phase was 45.7 pM-FXa/min for the lipid phase, 138.9 pM-FXa/min for the bulk aqueous phase, 554.7 pM-FXa/min for the lower viscous phase, and 40 pM-FXa/min for the resuspended pellet. Background levels were approximately 20 pM-FXa/min.

In a separate experiment, the immuno-capture procedure was omitted and plasma samples were relipidated directly with phospholipid (75 µM) and n-octyl-β-D-glucopyranoside. The detergent was dialyzed out and TF activity was measured as described above. There was no increase in the concentration of FXa with time, indicating that the TF present was either in an inactive form or inhibited.

EXAMPLE 2

Identification of alt-hTF mRNA in a Human Cell Line

The presence of TF mRNA was examined in a human cell line HL-60 using RT-PCR. A pair of primers designated "Forward" and "Reverse" (corresponding to bases 494–517 and 880–901, respectively, of the published TF cDNA sequence; GenBank accession number J02931) yielded two bands. The size of the larger band was approximately 400 base pairs—as expected from the TF cDNA sequence. The size of the smaller band was approximately 240 base pairs. The smaller band was subcloned and sequenced. Sequencing results revealed a previously unknown splicing variant of TF mRNA in which exon 5 is absent and exon 4 is thus fused directly with exon 6. Of note, such a fusion creates a frameshift in the TF open reading frame. To verify that this alternatively spliced TF mRNA contains all other components of the TF open reading frame, RT-PCR of HL-60 RNA was performed using a pair of primers designated "ORF21" and "ORF20" (corresponding to bases 90–110 and 1001–1020, respectively, of the published TF cDNA sequence; GenBank accession number J02931). The product(s) generated by these primers should contain the entire TF open reading frame. Two products were generated with primers ORF21 and ORF20; the lengths of these products were approximately 930 and 770 base pairs. This result is consistent with a notion that the alternatively spliced hTF mRNA, while missing exon 5, contains all the other components of the TF open reading frame. The 770 base pair product was subcloned and sequenced. The results of sequencing confirmed the existence of the TF mRNA spieces encoding an open reading frame with the initiation codon corresponding to bases 112–114, and a termination codon corresponding to bases 986–988 of the published TF cDNA sequence; GenBank accession number J02931.

The alternatively spliced hTF mRNA lacks exon 5 and thus contains a frameshift. The open reading frame of the alt-hTF mRNA encodes a human tissue factor variant whose mature peptide comprises 206 amino acids. Amino acids 1–166 are identical to those of the known membrane bound human TF; however, the remaining 40 amino acids at the carboxy-terminus diverge from the known TF amino acid sequence. Of note, the carboxy-terminus of the alternatively spliced hTF contains a region with potential transmembrane properties.

EXAMPLE 3

Expression of alt-hTF in Various Tissues

In order to determine whether the alternatively spliced hTF mRNA is expressed in various tissues, a BLAST search of EST libraries was conducted for the presence of clones that contain the site of alternative splicing, i.e. the end of exon 4 fused directly with start of exon 6. Four EST clones have been identified, and their sequences were analyzed for the presence of open reading frames using the Translate tool available at http://www.expasy.ch/tools/dna.html.

The lengths of reported sequences of the three clones derived from a human lung cDNA library (BG506479, BG539133, and BG546020) are 663, 780, and 747 base pairs, respectively. None of the three sequences encode a significantly larger non-interrupted stretch of amino acids in any of the three 5'–3' frames. Although all three sequences contain a region corresponding to the site of alternative splicing, i.e., TCA GGA AAG AAA TAT TCT (SGKKYS) (SEQ ID NO:3), in all three sequences this region is not in frame with the sequence encoding human tissue factor protein. The three clones corresponding to the above lung ESTs were obtained from the I.M.A.G.E. consortium and fully sequenced. None of the clones contained the complete alt-hTF open reading frame. However, sequencing results revealed that, like in membrane-bound TF mRNA, the long 3'-untranslated end of the asHTF mRNA is entirely encoded by exon 6.

The length of the reported sequence of a clone derived from a primary human keratinocyte cDNA library (BF149254) is 356 base pairs. This sequence encodes a stretch of amino acids 72 through 166 of the membrane bound human tissue factor fused to the first 23 amino acids of the 40 amino acid carboxyl-terminus unique to the alternatively spliced hTF. This sequence is, therefore, a partial (incomplete) cDNA encoding an alternatively spliced human tissue factor molecule.

EXAMPLE 4

Characterization of Plasma Depleted of the alt-hTF Protein

Frozen human plasma (300 mL) was thawed on ice and centrifuged at 3,000×G for 90 minutes. The supernatant (referred to as "start plasma") was passed at 4° C. through a column loaded with Affigel-coupled antibodies to the last 10 amino acids at the carboxyl-terminus of the alt-hTF protein. A flow-through sample was collected after 250 mL of start plasma was passed through the column.

Figure 3:
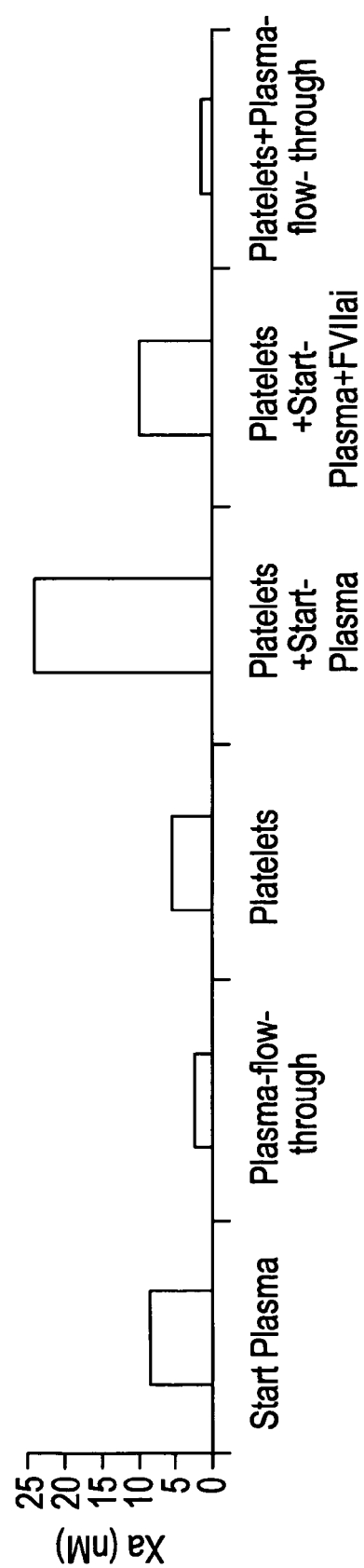
FIG. 3 is a graph of TF activity in human plasma treated with an antibody to alt-hTF.

Samples described above were tested for tissue factor activity using a Xa chromogenic assay in a platelet-shear system. Freshly drawn citrated blood was centrifuged at 135×G for 20 minutes at room temperature to prepare platelet rich plasma (PRP). Platelets were then pelleted by centrifuging PRP at 850×G for 12 minutes, washed twice in CGSa, and resuspended at 3×10$^8$ platelets/mL in modified Tyrode's Buffer. 75 µL of the test samples (i.e. start plasma and plasma-flow-through) were mixed with 75 µL of the platelet suspension. Platelets were activated with ADP (final concentration=1 mM) and recalcified (CaCl$_2$; final concentration=5 mM) prior to mixing with test samples. The plasma-platelet suspension was loaded into collagen-coated wells. A micro cone and plate viscometer were used to shear this plasma-platelet suspension at 650 s$^{-1}$ shear rate for 10 minutes after which a reaction mixture containing FX (final concentration=100 nM), FVIIa (final concentration=10 nM), and CaCl$_2$ (final concentration=5 mM) was added to the samples. 5 minutes after addition of the reaction mixture, the samples were assayed for Xa generation in the following manner. 25 µL of the test samples were added to the well of a 96 well plate containing EDTA (final concentration=25 mM). A chromogenic substrate of Factor Xa, Spectrozyme Xa, was then added to the well (final concentration=0.5 mM), and the plate was read for 15 minutes at 405 nm. The results are shown in FIG. 3. The start plasma, the flow-through sample, as well as platelet samples had little Xa activity. Upon addition of platelets and application of shear forces, the start plasma generated significant amounts of Xa (~23 nM). FVIIai inhibited this activity by about 60%. The flow-through sample, upon incubation with platelets as well as shear, generated insignificant amounts of Xa (~0.8 nM).

EXAMPLE 5

Expression of the alt-hTF Protein in Bacteria

The region encoding the entire mature peptide of the alternatively spliced hTF variant was amplified using RT-PCR and subcloned into pBAD/gIIIA expression vector (Invitrogen Corporation). The sequence of this construct was verified, and the recombinant alternatively spliced hTF protein was produced in E. coli. At the N-terminus of the expressed protein, three additional amino acids (i.e. Thr, Met, and Ala) were present due to the structure of the multiple cloning site in pBAD/gIIIA expression vector. The expressed protein was isolated from bacteria by osmotic shock, and the resultant osmotic shock fluid was concentrated via centrifugation in Centricon™ filter devices (Millipore). Presence of the desired protein in the concentrated osmotic shock fluid was verified by Western immunoblotting, and protein concentration was analysed using Bradford protein microassay.

Three samples containing the recombinant alt-hTF protein were then prepared: a sample of the protein dissolved in HBS, a sample of the relipidated protein, and a sample of the protein incubated with phospholipid vesicles. Relipidation of the recombinant protein was carried out as follows. 35 µg of protein in TBS were combined with n-octyl-β-D-glucopyranoside (final concentration—125 mM) and a phospholipid mixture (PS:PC 30:70, final concentration—75 µM) to the final volume of 0.5 mL. The sample was placed on orbital mixer (set to slow) for 30 min at RT, transferred into a 0.5 mL dialysis cassette and dialyzed overnight versus 2 L of TBS. Incubation of the recombinant protein with phospholipid vesicles was carried out as follows. 35 µg of protein in HBS were combined with a phospholipid vesicle preparation (PS:PC 30:70, final concentration—75 µM) that was extruded to yield vesicles with the diameter of 100 nm. This mixture was incubated overnight at room temperature.

The activity of relipidated alt-hTF, alt-hTF incubated with phospholipid vesicles, and plain alt-hTF was measured in the following manner. 8 µg of the protein were combined with a reaction mixture containing FX (final concentration=100 nM), FVIIa (final concentration=10 nM), and CaCl$_2$ (final concentration=5 mM). 5 minutes after adding the reaction mixture, 25 µl of the resultant mixture were sampled and added to the well of a 96 well plate containing EDTA (final concentration=25 mM). A chromogenic Xa substrate, Spectrozyme Xa, was then added to the well (final concentration=0.5 mM), and the plate was read for 15 minutes at 405 nM.

Figure 4A:
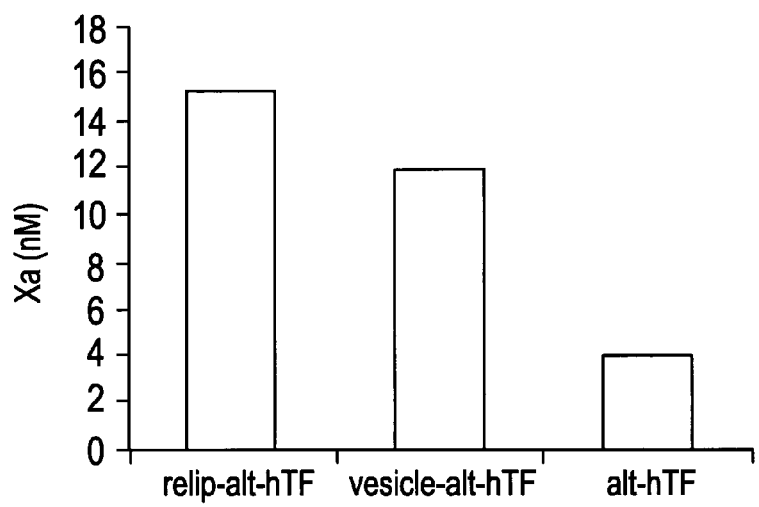
FIGS. 4A and 4B are graphs of recombinant alt-hTF activity in two assay systems.

The results of this assay are shown in FIG. 4A. Relipidated alt-hTF generated the largest amount of Xa (~14 nM). alt-hTF incubated with phospholipid vesicles also generated a substantial amount of Xa (~12 nM). Very small amounts of Xa were generated by the sample containing plain alt-hTF protein.

Activity of relipidated alt-hTF was also measured in a system involving addition of fresh platelets and application of shear forces. Platelets were prepared as follows. Freshly drawn citrated blood was centrifuged at 135×G for 20 minutes at room temperature to prepare platelet rich plasma (PRP). Platelets were then pelleted by centrifuging PRP at 850×G for 12 minutes, washed twice in CGSa, and resuspended at 3×10$^8$ platelets/ml in modified Tyrode's Buffer. Platelets were activated with ADP (final concentration=1 mM) and recalcified (CaCl$_2$; final concentration=5 mM). 8 µg of alt-hTF were mixed with 10$^8$ platelets/mL and loaded into collagen-coated wells. Polyclonal antibody to alt-hTF and FVII$_{ai}$ (TF inhibitor) were used as controls. In one sample, pAb-alt-hTF (final concentration=40 µg/mL) was mixed with the platelet-alt-hTF suspension. In another sample, FVII$_{ai}$ (final concentration=10 nM) was added to the alt-hTF-platelet mixture. A micro cone and plate viscometer were used to shear this protein-platelet suspension at 650 s$^{-1}$ shear rate for 10 minutes, after which a reaction mixture containing FX (final concentration=100 nM), FVIIa (final concentration=10 nM), and CaCl$_2$ (final concentration=5 mM) was added to the samples. 5 minutes after addition of the reaction mixture, the samples were assayed for X$_a$ generation in the following manner. 25 µL of the test samples were added to the well of a 96 well plate containing EDTA (final concentration=25 mM). A chromogenic Xa substrate, Spectrozyme Xa, was then added to the well (final concentration=0.5 mM), and the plate was read for 15 minutes at 405 nM.

Figure 4B:
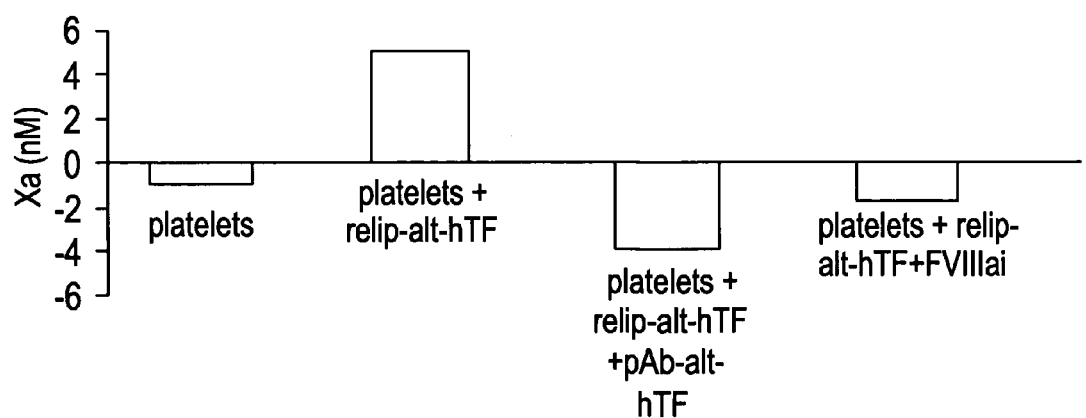

The results of this assay are shown in FIG. 4B. A suspension of isolated platelets, platelets mixed with the relipidated alt-hTF protein, as well as the polyclonal antibody to this protein and the platelet-alt-hTF suspension treated with FVIIai exhibited no Xa generation. When relipidated alt-hTF was mixed with platelets and sheared, a significant amount of Xa (~5 nM) was generated.

EXAMPLE 6

Presence of the alt-TF Protein in ex-vivo Thrombi

To determine which forms of TF are incorporated into ex-vivo thrombi, immunohistochemistry was performed on thrombi formed by shearing whole human blood over collagen-coated cover slips (650 s$^{-1}$). These thrombi stained with antibodies against alt-TF and sTF but stained only marginally, if at all, with an antibody specific for full-length TF, indicating that alt-hTF was selectively incorporated into thrombi formed under these conditions.

Modifications and variations of the alternatively spliced tissue factor, methods for manufacture, use and reagents for use therein, will be obvious to those skilled in the art from the foregoing description. Such modifications and variations are intended to come within the scope of the appended claims.

We claim:

1. An isolated alternatively spliced form of human tissue factor.

2. The tissue factor of claim 1 comprising Y S T S L E L W Y L W S S S L S S S W L Y L Y T S V E R Q E W G R A G R R T P H (SEQ ID NO:1).

3. The tissue factor of claim 1 comprising conservative amino acid substitutions.

4. An isolated human tissue factor protein comprising the sequence serine-serine-serine-leucine-serine-serine-serine (SEQ ID NO: 4).

5. The protein of claim 4 wherein the serines point outward having a high dielectric constant.

6. The protein of claim 4 wherein the serines point inward having a low dielectric constant.

7. An isolated nucleotide molecule encoding the tissue factor protein of claim 1.

8. The nucleotide molecule of claim 7 in a vector for expression of the tissue factor protein.

9. The nucleotide molecule of claim 8 in a vector for expression in a bacterial host.

10. The nucleotide molecule of claim 8 in a vector for expression in a eukaryotic host cell.

11. A method for making the tissue factor protein of claim 1 comprising expressing the nucleotide molecule of claim 8 in a suitable host cell in cell conditions permitting expression of the tissue factor protein and isolating the tissue factor protein therefrom.

12. An isolated double stranded RNA molecule comprising mRNA encoding the tissue factor protein of claim 1.

13. An isolated antibody that is specifically immunoreactive with the tissue factor protein of claim 1.

14. The antibody of claim 13 conjugated to a detectable label.

15. The antibody of claim 13 immobilized to a column or filter.

* * * * *